(12) United States Patent
Maruo et al.

(10) Patent No.: US 8,481,516 B2
(45) Date of Patent: Jul. 9, 2013

(54) CICLESONIDE CONTAINING STERILE AQUEOUS SUSPENSION

(75) Inventors: Susumu Maruo, Tokyo (JP); Kiyomi Ishida, Yamaguchi (JP)

(73) Assignee: Takeda GmbH, Constance (DE)

( * ) Notice: Subject to any disclaimer, the term of this patent is extended or adjusted under 35 U.S.C. 154(b) by 322 days.

(21) Appl. No.: 12/448,351

(22) PCT Filed: Dec. 26, 2007

(86) PCT No.: PCT/JP2007/075396
§ 371 (c)(1),
(2), (4) Date: Aug. 21, 2009

(87) PCT Pub. No.: WO2008/078842
PCT Pub. Date: Jul. 3, 2008

(65) Prior Publication Data
US 2010/0009951 A1    Jan. 14, 2010

(30) Foreign Application Priority Data

Dec. 27, 2006   (JP) .................................. 2006-351766

(51) Int. Cl.
*A61K 31/58* (2006.01)
*A61P 11/02* (2006.01)
*A61P 37/08* (2006.01)
*A61P 27/02* (2006.01)

(52) U.S. Cl.
USPC ............. 514/174; 514/171; 422/26; 424/400

(58) Field of Classification Search
None
See application file for complete search history.

(56) References Cited

U.S. PATENT DOCUMENTS

| 3,962,430 A | 6/1976 | O'Neill |
| 2004/0023935 A1 * | 2/2004 | Banerjee et al. ............. 514/174 |

FOREIGN PATENT DOCUMENTS

| JP | 8-187280 A | | 7/1996 |
| JP | 8-295622 A | | 11/1996 |
| WO | WO 90/14110 | * | 5/1990 |
| WO | 01/28563 A1 | | 4/2001 |
| WO | 2004/004739 A1 | | 1/2004 |
| WO | WO 2004/004439 | * | 1/2004 |
| WO | 2004/019955 A1 | | 3/2004 |

OTHER PUBLICATIONS

Stabilizing and Suspending Agents at http://pharphar.com/Stabilising_and_Suspending_Agents/4152.htm).*
Avicel® RC-591 at www.signetchem.com/downloads/datasheets/Fmc-biopolymer/Avicel-RC-591-Specifications.pdf).*
Kikuchi et al. In Journal of Controlled Release 47 21-29 (1997).*
Ratner et al. in the Journal of Allergy and Clinical Immunology 118(5) 1142-1148 (2006) (available online Sep. 26, 2006).*
Juarez et al. in International Journal of Pharmaceutics 216 (2001) 115-125).*
Jansson et al. in European Journal of Pharmaceutics and Biopharmaceutics 59 (2005) 557-564.*
Chapter 1 of "Microgel Suspensions: Fundamentals and Applications"; Edited by Alberto Fernandez-Nieves, Hans M. Wyss, Johan Mattsson, and David A. Weitz; Copyright 2011; Wiley-VCH Verlag GmbH & Co. KGaA, Weinheim; ISBN: 978-3-527-32158-2.
Mealy, N.E. et al., "Ciclesonide", Drugs of the Future, 2001, pp. 1033-1039, vol. 26, No. 11, Prous Science, Barcelona, Spain.

* cited by examiner

*Primary Examiner* — Dennis Heyer
(74) *Attorney, Agent, or Firm* — Nath, Goldberg & Meyer; Sheldon M. McGee

(57) ABSTRACT

The present invention relates to a sterile aqueous suspension containing ciclesonide, a microgel and a water soluble ionic polymer. The present invention provides a sterile aqueous suspension in which ciclesonide is dispersed homogeneously over a long period of time.

5 Claims, No Drawings

CICLESONIDE CONTAINING STERILE AQUEOUS SUSPENSION

This application is filed under 35 U.S.C. 371 as the national stage of PCT/JP2007/075396, filed Dec. 26, 2007, which claims priority to JP 2006-351766, filed Dec. 27, 2006.

TECHNICAL FIELD

The present invention relates to a sterile aqueous suspension of ciclesonide and the use thereof in the manufacture of medicaments.

BACKGROUND ART

Formulations that can be administered directly to the mucous membrane, such as nasal formulations for the treatment of allergic rhinitis and ophthalmic formulations for the treatment of dry eyes, have been developed to enhance absorption efficiency and pharmacological efficacy of drugs. In these formulations for administration to the mucous membrane an aqueous base is used to avoid irritation to the tissues. Since active ingredients are generally only slightly soluble in the aqueous base, they are often used in form of an aqueous suspension. In addition, aqueous formulations generally contain antiseptics and/or preservatives to inhibit bacterial growth. The use of these antiseptics and/or preservatives in drugs that are used over a long period of time is not preferable in terms of adverse drug reactions to the mucous tissues. Accordingly, safer antiseptics and preservatives have been developed and formulations containing no antiseptics or preservatives have been proposed.

As a method for obtaining so-called sterile formulations that contain no antiseptics or preservatives, sterilization, for example, autoclave sterilization, radiation sterilization, and sterilization by filtration are generally utilized. Various problems occur, however, when these sterilization methods are to be simply applied to manufacturing of an aqueous suspension.

Aqueous suspensions generally contain, as an ingredient, a water soluble or water swellable polymer as a dispersant for dispersing a water insoluble or slightly water soluble active ingredient homogeneously over a long period of time. Thus, when an aqueous suspension is attempted to be obtained by sterilization, for example, autoclave sterilization, radiation sterilization or sterilization by filtration, the structure of these dispersants is destroyed so that problems of safety and long-term dispersion stability of the suspension occur. In this respect, a method in which autoclave sterilization is performed under conditions where salt is contained at a saturation concentration or higher followed by dilution to obtain a sterile aqueous suspension (U.S. Pat. No. 3,962,430) and a method in which an aqueous solution containing 15% to 40% of a polyhydric alcohol is subjected to autoclave sterilization to obtain a sterile aqueous suspension (Japanese Patent Laid-open No. 8-187280) have been proposed. The addition of these additive ingredients causes various problems, however, such as a decrease in absorption of the drug through the mucous membrane or induction of irritability to the mucous membrane.

On the other hand, when a sterile aqueous suspension is attempted to be obtained by sterilization by filtration, the suspension must have an appropriately low viscosity to be filtered through a 0.22 μm sterile filter. There is thus a problem that when the viscosity of a formulation is reduced, homogeneous dispersion of a water insoluble or slightly water soluble drug is deteriorated during storage over a long period of time. In this regard, an aqueous suspension from which a drug is precipitated but which has an excellent redispersibility has been proposed (Japanese Patent Laid-open No. 8-295622). There is a problem, however, that when the suspension is shaken for redispersion of a drug upon administration, entrapment of air bubbles occurs to deteriorate quantitative dispensing of the drug.

DISCLOSURE OF THE INVENTION

Problems to be Solved by the Invention

An object of the present invention is to provide a sterile aqueous suspension in which ciclesonide remains dispersed homogeneously over a long period of time (preferably 3 years that are generally required for drugs). The present inventors have eagerly studied to achieve these objects, and have found that these objects can be achieved using a microgel and a water soluble ionic polymer for an aqueous suspension that is obtained by dispersing ciclesonide with a dispersant, and completed the present invention.

Means for Solving the Problems

In other words, the present invention relates to a sterile aqueous suspension comprising ciclesonide, a microgel and a water soluble ionic polymer.

According to the present invention, the microgel is preferably a microgel obtained by microgelation of a water soluble polymer by crosslinking, and more preferably a microgel obtained by microgelation of at least one selected from the group consisting of gellan gum, carrageenan, sodium alginate, agar, xanthan gum and gelatin by crosslinking.

According to the present invention, the water soluble ionic polymer is preferably at least one selected from the group consisting of carmellose sodium, sodium hyaluronate and polylysine.

BEST MODE OF CARRYING OUT THE INVENTION

The present invention relates to a sterile aqueous suspension comprising ciclesonide, a microgel and a water soluble ionic polymer.

According to the present invention, the microgel is used as a dispersant. A substance capable of forming the microgel is not particularly limited, as long as it is water soluble and its viscosity increases with microgelation.

The microgel is preferably a microgel obtained by microgelation of a water soluble polymer by cross-linking. Specific examples of the water soluble polymer capable of microgelation include gellan gum, carrageenan, sodium alginate, agar, pectin, gelatin, xanthan gum, polyvinyl alcohol, sodium polyacrylate, and alkyl polyacrylate esters. In view of easiness of microgelation and safety as a drug, water soluble polymers capable of gelation by intermolecular bonding via a noncovalent bond, such as a hydrogen bond or an electrostatic (ionic) bond, are preferable, and among them, gellan gum, carrageenan, sodium alginate, agar, xanthan gum and gelatin are more preferable.

Examples of the microgelation method include a method in which a polymer is crosslinked via a covalent bonding such as photocrosslinking, thermal crosslinking, or radiation crosslinking while stirring to achieve gelation or a method in which a polymer is crosslinked via an intermolecular bond such as a hydrogen bond, an electrostatic (ionic) bond, a hydrophobic bond, or a chelate bond to achieve gelation.

Since it is preferable for the microgel to be highly safe when used in a drug, the method of gelation by crosslinking via an intermolecular bond such as a hydrogen bond, an electrostatic (ionic) bond, a hydrophobic bond, or a chelate bond is more preferable.

The particle size of the microgel is not particularly limited, as long as it is in the range where the microgel exhibits flowability. It is preferably 0.01 µm to 1000 µm, and more preferably 0.1 µm to 500 µm, however, for example, in terms of homogeneity onto the mucous membrane upon administration as ophthalmic formulation or nasal formulation and easiness in manufacturing.

The concentration of the water soluble polymer capable of microgelation is not particularly limited, as long as the concentration after microgelation is such that the microgel can be sterilized by filtration when dissolved in water, dispersion homogeneity of a drug can be maintained over a long period of time and the viscosity is suitable for administration to the mucous membrane. Generally, the concentration of the water soluble polymer capable of microgelation in the formulation is preferably 0.001% by weight to 20% by weight, and more preferably 0.01% by weight to 10% by weight.

In addition, according to the present invention, it is important to use a water soluble ionic polymer as a wetting agent for ciclesonide. The water soluble ionic polymer used in the present invention is not particularly limited, as long as it can be sterilized by filtration. Specific examples of the water soluble ionic polymer include carmellose sodium, sodium hyaluronate, polylysine, sodium polyglutamate, sodium polyaspartate, polyethyleneimine, chitosan, sodium polyacrylate, polyoxyethylene amine, a methyl vinyl ether-maleic anhydride copolymer, or a methylene-sodium β-naphthalenesolfonate copolymer. Among these, carmellose sodium, sodium hyaluronate, and polylysine are particularly preferable in terms of high thixotropic properties, high safety, and economic efficiency.

When conventionally known surfactants such as polyoxyethylene 20 sorbitan monooleate (Tween 80) and glycerol stearate or non-ionic polymers such as hydroxypropyl cellulose, hydroxypropylmethyl cellulose, and polyethylene glycol are used as a wetting agent for a drug, it is difficult to maintain homogenous dispersion of ciclesonide over a long period of time.

The concentration of the water soluble ionic polymer as a wetting agent is determined as an amount that is required to inhibit adhesion of ciclesonide to a container or disperse ciclesonide homogeneously, and determined depending on the amount of ciclesonide required for treatment. Generally, the concentration of the water soluble ionic polymer in the formulation is preferably 0.01% by weight to 10% by weight. Also, the concentration of the water soluble ionic polymer is preferable as 0.1 time to 20 times as the drug concentration in terms of a function as a wetting agent and economic efficiency.

The general manufacturing method of the sterile aqueous suspension of ciclesonide according to the present invention can be conducted by (i) a step of forming a microgel after performing sterilization by filtration of a water soluble polymer solution capable of microgelation; (ii) a step of predispersing ciclesonide in an aqueous ionic polymer solution sterilized by filtration; and (iii) a step of mixing the microgel and the aqueous ionic polymer solution in which ciclesonide is predispersed. A sterile aqueous suspension of ciclesonide can be prepared by this method.

The step (i) of forming a microgel can be performed as follows. When microgelation is performed by crosslinking via an electrostatic (ionic) bond or a coordination bond, a water soluble polymer capable of microgelation is dissolved in sterile purified water, the resultant solution is subjected to sterilization by filtration, then an aqueous solution of a polyion (for example, an aqueous solution of calcium chloride) is added under stirring with heating, and the resultant mixture is cooled to room temperature while stirring with a high shear stirrer such as a homomixer. When microgelation is performed by crosslinking to form an intermolecular crosslinkage by hydrogen bonding, a water soluble polymer capable of microgelation is dissolved in sterile purified water with heating, and the resultant solution is subjected to sterilization by filtration and then cooled to room temperature while stirring. When microgelation is performed by crosslinking via a hydrophobic bond, a water soluble polymer capable of microgelation is dissolved in sterile purified water, the resultant solution is subjected to sterilization by filtration, an aqueous solution containing a micelle-forming ingredient such as phospholipid or a non-ionic surfactant is added to the sterilized solution while stirring, and the resultant mixture is stirred with a high shear stirrer such as a homomixer. The microgel can be prepared by these methods.

The step (ii) of predispersing ciclesonide in an aqueous ionic polymer solution can be performed by dissolving a water soluble ionic polymer in sterile purified water, subjecting the resultant solution to sterilization by filtration, and then adding ciclesonide to the sterilized solution while stirring. The aqueous ionic polymer solution in which ciclesonide is dispersed can be prepared by this method.

Further, the water soluble ionic polymer may be added separately in two steps, in the step (ii) of predispersing ciclesonide and in the subsequent step (iii) of mixing the microgel with the aqueous ionic polymer solution in which ciclesonide is predispersed. In this case, since the amount of the water soluble ionic polymer to be dissolved upon predispersion can be reduced and the ionic polymer present at a low concentration in a predispersion solution can be subjected to sterilization by filtration, this method is effective when the concentration of the water soluble ionic polymer is high. In addition, a sterile formulation having the final composition unchanged can be obtained by separately adding the remaining water soluble ionic polymer in the step (iii).

The step (iii) of mixing the microgel and the aqueous ionic polymer solution in which ciclesonide is predispersed can be performed by stirring the microgel and the ionic polymer solution in which ciclesonide is predispersed with a high shear stirrer such as a homomixer. The sterile aqueous suspension of ciclesonide according to the present invention can be prepared by this step.

The viscosity of the sterile aqueous suspension of ciclesonide is not particularly limited. In view of homogenous dispersion of ciclesonide, homogenous administration to the mucous membrane, and easiness of removal from a container, however, the viscosity is preferably 10 mPa·s to 10000 mPa·s, and more preferably 50 mPa·s to 2000 mPa·s.

The active ingredient used in the present invention is ciclesonide. Ciclesonide as used herein includes the compounds [11β,16α(R)]-16,17-[(cyclohexylmethylen)bis(oxy)]-11-hydroxy-21-(2-methyl-1-oxoprop-oxy)pregna-1,4-dien-3,20-dione (the R epimer), [11β,16α(S)]-16,17-[(cyclohexylmethylen)bis(oxy)]-11-hydroxy-21-(2-methyl-1-oxopropoxy)-pregna-1,4-dien-3,20-dione (the S epimer), mixtures of the two foregoing compounds in any ratio (epimer mixtures), pharmaceutically acceptable salts thereof, solvates of the compounds and the salts thereof, and physiologically functional derivatives of the compounds, salts and solvates thereof. Ciclesonide and its preparation are disclosed e.g. in DE 4129535 and WO 9809982. By the term "physiologically functional derivative" is meant a chemical derivative of ciclesonide having the same physiological function as ciclesonide, for example, by being convertible in the body thereto or by being an active metabolite of ciclesonide. Physiological functional derivatives of ciclesonide which may be mentioned in connection with the invention are, for example, the 21-hydroxy derivatives of ciclesonide with the chemical names 16α,17-(22R,S)-cyclohexylmethylendioxy-11β,21-dihydroxy-pregna-1,4-dien-3,20-dione, 16α,17-(22S)-cyclohexylmethylendioxy-11β,21-dihydroxy-pregna-1,4-dien-3,20-dione and in particular 16α,17-(22R)-cyclohexylmethylendioxy-11β,21-dihydroxy-pregna-1,4-dien-3,20-dione. These compounds and their preparation are disclosed e.g. in WO 9422899.

The amount of ciclesonide in the present invention is a therapeutically effective dose, and can be determined, for example, in accordance with the kind and severity of the disease, age and body weight of a patient. Preferably, the concentration of ciclesonide in the aqueous suspension of the present invention is from 0.01% by weight to 1% by weight, and more preferably the concentration of ciclesonide in the aqueous suspension of the present invention is from 0.01% by weight to 0.5% by weight, relative to the total amount of the composition.

In addition, the aqueous suspension may contain conventionally known additives such as stabilizers, anti-oxidants, pH adjusters, isotonic agents, and/or odor improvers, as required. Specific examples include stabilizers such as sodium edetate, and/or sodium citrate; anti-oxidants such as ascorbic acid, and/or tocopherol; pH adjusters such as hydrochloric acid, sodium hydroxide, and/or phosphate salts; isotonic agents such as salt, and/or glucose; and odor improvers such as menthol. They may be used alone or in a combination of two or more.

EXAMPLES

The present invention will be further illustrated referring to Examples, although the present invention is not restricted by the Examples. In Examples, parts and % refer to parts by weight and % by weight, respectively. Centrifugation stability was determined in the Examples for evaluation of dispersion stability during storage over a long period of time. One gram of an aqueous suspension was placed in a 8 mmΦ microvial, left standing for 20 hours, and then centrifuged at 600 rpm, 800 rpm, 1000 rpm, 2000 rpm, and 3000 rpm with a centrifuge for 10 minutes, respectively. After that, phase separation was evaluated by visual inspection.

Reference Example 1

A 0.2% aqueous gellan gum solution was prepared by dissolving 0.4 part of gellan gum in 199.6 parts of purified water. The 0.2% aqueous gellan gum solution thus obtained was pretreated at a shear speed of 200/s for 10 minutes and left standing for 2 hours. Then, the viscosity was measured with a rheometer (TA Instrument, AR-200) at a shear speed of 14.2/s at 25° C. The viscosity was 5 mPa·s. The solution was easily sterilized by filtering through a 0.22 μm filter. While 200 parts of the 0.2% aqueous gellan gum solution was stirred at 90° C., 1.5 parts of a 400 mM aqueous calcium chloride solution that had been sterilized by filtering through a 0.22 μm filter was added thereto. The resultant mixture was cooled to room temperature while stirring at 12000 rpm with a homomixer for 30 minutes to prepare a sterile microgel. The viscosity of the microgel thus obtained was measured with a rheometer. The viscosity was 137 mPa·s. It was thus confirmed that the microgel had a viscosity suitable for dispersing a drug homogeneously over a long period of time.

Solutions of a water soluble polymer capable of microgelation such as carrageenan, sodium alginate, agar, xanthan gum, and gelatin can be sterilized by filtration, like gellan gum. A sterile microgel can be thus prepared by microgelation of a water soluble polymer capable of microgelation that has been sterilized by filtration, by mixing the solution with an aqueous calcium chloride solution that has been sterilized by filtration or other suitable methods.

Example 1

While 200 parts of a 0.2% aqueous gellan gum solution was stirred at 90° C., 1.5 parts of a 400 mM aqueous calcium chloride solution was added, and the resultant mixture was cooled to room temperature while stirring at 12000 rpm with a homomixer for 30 minutes to prepare microgel. An aliquot of 0.8 part of carmellose sodium was dissolved in 19.2 parts of purified water, and 0.11 part of ciclesonide was added to and predispersed in the resultant solution with a propeller mixer. The resultant dispersion was added to the microgel solution and the resultant mixture was stirred at 10000 rpm with a homomixer for 10 minutes to obtain an aqueous suspension.

After 1 g of the aqueous suspension thus obtained was placed in a microvial and left standing for 24 hours, centrifugation stability was evaluated using a centrifuge. The results are shown in Table 1. As shown in Table 1, no phase separation was observed and good centrifugation stability was shown.

In the table, "wt %" represents a concentration of each ingredient of the formulation.

TABLE 1

| Ingredient | Example 1 | Comparative Example 1 | Comparative Example 2 | Comparative Example 3 |
| --- | --- | --- | --- | --- |
| Gellan gum (wt %) | 0.18 | 0.20 | 0.18 | 0.18 |
| Carmellose sodium (wt %) | 0.36 | — | — | — |
| Tween 80 (wt %) | — | — | 0.36 | — |
| Hydroxypropylmethyl cellulose (wt %) | — | — | — | 0.36 |
| Ciclesonide (wt %) | 0.05 | 0.05 | 0.05 | 0.05 |
| Calcium chloride (wt %) | 0.03 | 0.03 | 0.03 | 0.03 |
| Purified water (wt %) | 99.38 | 99.72 | 99.38 | 99.38 |
| Centrifugation stability | No phase separation | Remarkable adhesion of ciclesonide to the container | Phase separation present | Phase separation present |

Comparative Example 1

Aqueous suspensions were obtained as in Example 1, expect that the formulation composition was changed as shown in Table 1 and that ciclesonide was directly added to the microgel without using an aqueous solution of a water soluble ionic polymer to prepare an aqueous suspension containing only the microgel but not containing a wetting agent. As shown in Table 1, in the aqueous suspension containing only the microgel, marked adhesion of ciclesonide to the container was observed.

Comparative Examples 2 and 3

Aqueous suspensions were obtained as in Example 1, except that the formulation composition was changed to those shown in Tables 1.

As shown by Comparative Examples 2 and 3 in Table 1, phase separation was observed in centrifugation stability evaluation for the aqueous suspensions in which a surfactant or a water soluble non-ionic polymer was used as a wetting agent for ciclesonide in place of the water soluble ionic polymer.

INDUSTRIAL APPLICABILITY

According to the present invention, a sterile aqueous suspension in which ciclesonide remains dispersed homogenously over a long period of time can be obtained by mixing a microgel obtained by subjecting a water soluble polymer capable of microgelation to sterilization by filtration followed by crosslinking, for example, via an electrostatic (ionic) bond, or a hydrogen bond to form the microgel and to increase its viscosity and a water soluble ionic polymer as a wetting agent for ciclesonide.

The invention claimed is:

1. A sterile aqueous suspension comprising water, ciclesonide, a polyion, a microgel and a water-soluble ionic polymer, wherein the microgel is obtained by microgelation of at least one water soluble polymer selected from the group consisting of gellan gum, carrageenan, agar, pectin, xanthan gum, gelatin, polyvinyl alcohol, sodium polyacrylate and alkyl polyacrylate esters by cross-linking via an electrostatic (ionic) bond or a coordination bond.

2. The sterile aqueous suspension according to claim 1, wherein the water-soluble ionic polymer is at least one selected from the group consisting of carmellose sodium, sodium hyarulonate and polylysine.

3. The sterile aqueous suspension according to claim 1, wherein ciclesonide is the compound [11β,16α(R)]-16,17-[(cyclohexylmethylen)bis(oxy)]-11-hydroxy-21-(2-methyl-1-oxoprop-oxy)pregna-1,4-dien-3,20-dione.

4. A process for preparing a sterile aqueous suspension according to claim 1 comprising the steps of
   (i) forming a microgel after performing sterilization by filtration of a water soluble polymer solution capable of microgelation,
   (ii) predispersing ciclesonide in an aqueous ionic polymer solution sterilized by filtration,
   (iii) mixing the microgel and the aqueous ionic polymer solution in which ciclesonide is predispersed.

5. A method for treating allergic rhinitis in a patient comprising administering to a patient in need thereof a sterile aqueous suspension according to claim 1 in a therapeutically effective amount.

* * * * *